United States Patent
Diamant et al.

(10) Patent No.: US 9,498,237 B2
(45) Date of Patent: Nov. 22, 2016

(54) METHOD AND SYSTEM FOR DESTROYING OF UNDESIRABLE FORMATIONS IN MAMMALIAN BODY

(71) Applicant: Lithotech Medical Ltd., Katzrin (IL)

(72) Inventors: Valery Diamant, Katzrin (IL); Alexey Dutov, Tomsk (RU); Vladimir Chernenko, Tomsk (RU); Marat Lerner, Tomsk (RU)

(73) Assignee: LITHOTECH MEDICAL LTD (IL)

( * ) Notice: Subject to any disclaimer, the term of this patent is extended or adjusted under 35 U.S.C. 154(b) by 145 days.

(21) Appl. No.: 14/297,982

(22) Filed: Jun. 6, 2014

(65) Prior Publication Data

US 2014/0288571 A1    Sep. 25, 2014

Related U.S. Application Data

(63) Continuation of application No. 12/711,803, filed on Feb. 24, 2010, now Pat. No. 8,777,963.

(51) Int. Cl.
*A61B 17/22*    (2006.01)
*A61B 17/00*    (2006.01)
*A61B 18/00*    (2006.01)

(52) U.S. Cl.
CPC ..... *A61B 17/22022* (2013.01); *A61B 17/2202* (2013.01); *A61B 90/98* (2016.02);
(Continued)

(58) Field of Classification Search
CPC .............. A61B 17/2202; A61B 17/22022; A61B 2019/4815; A61B 2018/00988
USPC .................. 606/113, 114, 127, 128; 601/1–4
See application file for complete search history.

(56) References Cited

U.S. PATENT DOCUMENTS 2,559,227 A    7/1951  Rieber
3,735,764 A  * 5/1973  Balev .................... G10K 15/06
                                                  601/4
(Continued)

FOREIGN PATENT DOCUMENTS

CA    2104414 A1    2/1995
DE    3633527 A1    4/1988
(Continued)

OTHER PUBLICATIONS

Device for Contact Electrospulse Lithotripsy (UROLITH), Technical Specification and Operation Manual, MedLine Ltd., Tomsk, Russia, medline@mail.tomsknet.ru, 16 pgs.
(Continued)

*Primary Examiner* — Kathleen Holwerda
(74) *Attorney, Agent, or Firm* — Blank Rome LLP

(57) ABSTRACT

A method and a system for destruction of an undesirable formation in a mammalian body are described. The invention is based on inserting a probe into mammalian body; said probe is electrically connectable to a control unit and upon bringing the probe in physical contact with the formation supplying pulses of energy from the control unit to the probe in order to destroy the formation. The invention further comprises counting amount of pulses being supplied to the probe and establishing a remaining service life of the probe by subtracting the amount of pulses being supplied to the probe from an amount of pulses corresponding to initial service life of the probe. The treatment session is automatically terminates as soon as amount of pulses being supplied to the probe approaches at least a fraction of the established remaining service life of the probe. The established remaining service life of the probe is stored for new treatment session. Delivery of pulses automatically terminates when the remaining service life is exhausted and use of such probe becomes impossible.

8 Claims, 12 Drawing Sheets

(52) U.S. Cl.
CPC ............... *A61B2017/00185* (2013.01); *A61B 2017/00194* (2013.01); *A61B 2017/00199* (2013.01); *A61B 2017/00477* (2013.01); *A61B 2017/22021* (2013.01); *A61B 2018/00988* (2013.01); *A61B 2090/0803* (2016.02)

(56) References Cited

U.S. PATENT DOCUMENTS

| | | | |
|---|---|---|---|
| 3,982,541 | A | 9/1976 | L'Esperance, Jr. |
| 4,055,783 | A | 10/1977 | Walters et al. |
| 4,308,905 | A | 1/1982 | Gallagher |
| 4,605,003 | A | 8/1986 | Oinuma et al. |
| 4,654,024 | A | 3/1987 | Crittenden et al. |
| 4,665,476 | A * | 5/1987 | Masuda ............... B03C 3/68 323/903 |
| 4,722,340 | A * | 2/1988 | Takayama ........ A61B 17/22022 601/4 |
| 4,927,427 | A | 5/1990 | Kriauciunas et al. |
| 5,009,656 | A | 4/1991 | Reimels |
| 5,254,121 | A | 10/1993 | Manevitz et al. |
| 5,350,375 | A | 9/1994 | Deckelbaum et al. |
| 5,419,767 | A | 5/1995 | Eggers et al. |
| 5,448,363 | A | 9/1995 | Hager |
| 5,722,980 | A | 3/1998 | Schulz et al. |
| 6,007,514 | A | 12/1999 | Nita |
| 6,149,656 | A | 11/2000 | Walz et al. |
| 6,261,298 | B1 | 7/2001 | Irion et al. |
| 6,264,653 | B1 | 7/2001 | Falwell |
| 6,319,261 | B1 | 11/2001 | Bowers |
| 7,087,061 | B2 * | 8/2006 | Chernenko ...... A61B 17/22022 604/22 |
| 7,568,619 | B2 | 8/2009 | Todd et al. |
| 8,777,963 | B2 * | 7/2014 | Diamant ............ A61B 17/2202 601/4 |
| 2003/0176873 | A1 | 9/2003 | Chernenko et al. |
| 2005/0143724 | A1 * | 6/2005 | El-Galley .......... A61B 18/1402 606/34 |
| 2006/0129140 | A1 | 6/2006 | Todd et al. |
| 2007/0021754 | A1 | 1/2007 | Chernenko et al. |
| 2007/0085611 | A1 | 4/2007 | Gerry et al. |
| 2008/0015570 | A1 | 1/2008 | Ormsby et al. |
| 2008/0028860 | A1 | 2/2008 | Refko et al. |
| 2008/0147170 | A1 | 6/2008 | Vrba |
| 2008/0172067 | A1 | 7/2008 | Nita et al. |
| 2008/0294162 | A1 | 11/2008 | Rossetto et al. |
| 2009/0171278 | A1 | 7/2009 | Hirszowicz et al. |
| 2009/0192405 | A1 | 7/2009 | Carney |
| 2009/0209900 | A1 | 8/2009 | Carmeli et al. |
| 2010/0036294 | A1 | 2/2010 | Mantell et al. |

FOREIGN PATENT DOCUMENTS

| | | |
|---|---|---|
| DE | 3927260 A1 | 2/1991 |
| DE | 19609019 A1 | 9/1997 |
| DE | 19810696 C1 | 5/1999 |
| EP | 0467137 A2 | 1/1992 |
| JP | 3295549 A | 12/1991 |
| RU | 2348373 C1 | 3/2009 |
| RU | 2388427 C2 | 5/2010 |
| WO | WO-9710058 A1 | 3/1997 |
| WO | WO-03075777 A1 | 9/2003 |
| WO | WO-2007095498 A1 | 8/2007 |
| WO | WO-2008035349 A1 | 3/2008 |
| WO | WO-2008102346 A1 | 8/2008 |

OTHER PUBLICATIONS

Regularity of Solid Dielectric Breakdown at the Interface with Liquid Dielectric Under Action of Voltage Pulse, Russian Academy of Sciences, International Association of Scientific Discoveries Authors, Diploma No. 107 for the discovery, 3 pgs, English translation 2 pgs.
B.V. Semkin, A.F. Usov, V.I.Kurets, The Principles of Electric Impulse Destruction of Materials, Russian Academy of Sciences, 1995, Saint-Petersburg, Nauka, 1993, 8 pgs (English translation of passages marked).
The AUTOLITH Lithotriptor, Nortech Advanced Technology for Better Medicine, Lithotripsy Products, 1999 Northgate Technologies, Inc., Riwolith 2280, Instruction Manual, 11 pgs.
Method for intracorporeal lithotripsy fragmentation and apparatus for its implementation, Comments to Patent Application PCT/IL03/00191, 1 pg.
Office Action dated May 15, 2012, cited in U.S. Appl. No. 11/488,038.
Extended European Search Report dated Apr. 26, 2012, cited in EP Application No. 11150663.0.
European Search Report dated Jun. 1, 2011, cited in EP Application No. 11150665.5.
Richard Wolf, "Electrohydraulic Shock Wave Lithotripsy," Riwolith 228, 1 page, undated.
"Riwolith 2280," Instruction Manual, HA-D257/Index: 10-00-9.0 / AM:KG 00-248, 8 pages, undated.

* cited by examiner

METHOD AND SYSTEM FOR DESTROYING OF UNDESIRABLE FORMATIONS IN MAMMALIAN BODY

This application is a continuation of U.S. patent application Ser. No. 12/711,803, filed Feb. 24, 2010. The entire contents of this application is hereby incorporated by reference.

FIELD OF THE INVENTION

The present invention relates to medicine, namely to destroying of undesirable formations in mammalian body, in particular to fragmentation of calculi, appearing in ducts of human body. Even more particular the present invention refers to fragmentation by a probe, i.e. a lithotriptor having working head insertable within the body. The present invention is advantageous for example for shock-wave intracorporeal lithotripsy used for fragmentation, disintegration or otherwise destroying such formations like various stones in the body, e.g. gallstones, kidney stones, cystine stones and other calculi, appearing in the biliary or urinary system of human body.

It should be understood however that the present invention is not limited to the destroying of undesirable formations appearing merely in human body. It can be employed for treatment of animals as well.

Furthermore the present invention is not limited to destroying of undesirable formations of solely inorganic nature, like mineral calculi appearing in biliary or urinary system. It is suitable also for destroying of other foreign objects, or formations including those of inorganic and/or organic nature which might appear in mammalian body. Some examples of such undesirable formations comprise abnormal tissue causing arrhythmia, human atherosclerotic plaque, CTO (chronic total occlusion), etc.

BACKGROUND OF THE INVENTION

Shock-wave lithotripsy stone fragmentation treatment employs high-energy shock waves to fragment and disintegrate calculi and it can be broadly categorized according to the pattern of energy transfer to the calculi. In this connection lithotripsy can be classified as extracorporeal and intracorporeal.

Shock-wave extracorporeal lithotripsy is a process, which transfers energy needed for stone fragmentation in the form of shock waves from an outside source through body tissue to the calculi. Extracorporeal shock-wave lithotripsy (ESWL) has proven effective in achieving stone fragmentation.

However, since the energy wave transmission is indirect, and in order to carry out the treatment successfully it is required precise directional focusing of the energy at the stone through intervening body tissue. Imprecise focusing might be associated with damaging of the intervening tissues and therefore additional treatments might be required to take care of the damage.

Intracorporeal lithotripsy utilizes a probe advanced to and positioned in proximity to the calculus. The energy, required for fragmentation is transferred through the probe to the calculus and the treatment process can be visualized during fragmentation. The mode of energy transfer may be different and accordingly the intracorporeal lithotripsy techniques are divided into following groups: ultrasonic, laser, electro-hydraulic, electro-impulse and mechanic/ballistic impact.

The last group comprises, for example, detonating an explosive near the stone and causing the shock wave generated by the explosion to act directly upon the stone and crush it into pieces. An example of such technique is disclosed in U.S. Pat. No. 4,605,003, referring to a lithotriptor comprising an inner tube inserted within an outer slender tube and provided with an explosive layer or a gas-generating layer. By the blasting of the explosive layer or the gas-generating layer, the outer slender tube or the inner tube is caused to collide with the stone and crush it.

An example of mechanical impact technique can be found in U.S. Pat. No. 5,448,363 in which is disclosed an endoscopic lithotriptor provided with a hammer element to periodically strike the stone. The hammer element is pneumatically driven by a linear jet of air causing it to swing through an arc about a pivot to impact an anvil.

There are known also many other patents, disclosing lithotriptors, which operation is based on mechanic/ballistic principle, e.g. U.S. Pat. No. 5,722,980, U.S. Pat. No. 6,261,298.

An example of laser technique is described in U.S. Pat. No. 4,308,905, concerning multi-purpose lithotriptor, equipped with laser light-conducting fibers, through which the energy required for crushing the stone is conducted.

It should be pointed out that applying energy by laser is used not only for lithotripsy destroying of stones but also for destroying of other formations, e.g. abnormal tissues causing arrhythmia. An example of this procedure is disclosed in U.S. Pat. No. 6,264,653.

Ultrasonic technique is relatively popular and because of its safety and usefulness is widely accepted. According to this principle ultrasound probe emits high-frequency ultrasonic energy that has a disruption effect upon direct exposure to the stone.

Direct contact of the probe tip and stone is essential for effectiveness of ultrasonic lithotripsy. This technique is implemented in many lithotriptors, e.g. as described in U.S. Pat. No. 6,149,656.

Electro-hydraulic technique utilizes electric discharge, ignited between two electrodes disposed within the probe and producing shock wave, expanding towards the calculus through liquid phase, which surrounds the calculus. In the literature electro-hydraulic lithotripsy is defined as the oldest form of "power" lithotripsy. The electro-hydraulic lithotriptor releases high-energy impulse discharges from an electrode at the tip of a flexible probe, which is placed next to the stone. Since the discharge takes place within liquid phase the calculus is destroyed by virtue of combination of energy of the shock wave, caused by the discharge, hydraulic pressure of the surrounding liquid and collision of fragments in the liquid flow.

Below are listed some references, referring to intracorporeal lithotripting devices, utilizing the electro-hydraulic principle.

A typical electro-hydraulic lithotriptor is described in CA 2104414. This apparatus is intended for fracturing deposits such as urinary and biliary calculi as well as atherosclerotic plaque in the body. The lithotriptor comprises a flexible elongated guide member adapted for insertion within the body, means for supplying a working fluid, a hollow tube mounted on the distal end of the probe, means for initiating an electric spark within the hollow tube from an external energy source, capable of generating pulsed shock waves in the working fluid for impinging the stone and a nozzle, which is made of shock and heat resistant material and mounted on the distal end of the guide member. The nozzle is capable of directing the shock waves to a focal point for impinging the stone. The lithotriptor is provided also with optical viewing system.

In U.S. Pat. No. 2,559,227 is disclosed an apparatus for generating shock. The apparatus comprises a truncated ellipsoidal reflector for reflecting the shock waves and a cavity constituting a chamber for reflecting said shock waves. The cavity has the same truncated ellipsoidal shape, while one of the two focal points of the ellipsoid is disposed in the cavity opposite the truncated part. The cavity is filled with a liquid for transmitting the shock waves, for example oil. The apparatus is provided with a shock wave generator device, conventionally comprising two electrodes disposed at least partly inside said cavity. The two electrodes are arranged to generate an electric arc discharge at the focal point located in the cavity opposite the truncated part. The apparatus has also means for selectively and instantaneously delivering an electric voltage to two electrodes provoking electric arc discharge between said electrodes thus generating shock waves propagating through the liquid contained in the cavity.

The electrodes are made of highly conductive material such as copper or brass and are mounted on an insulator with possibility for adjusting the spacing therebetween.

In DE 19609019 is described an impact probe, provided with at least one electrode guided in the tube. The electrode acts on the object when the probe is longitudinally moved in the direction of the object e.g. a stone. Electro-hydraulic pressure wave is produced at the free end of the probe.

In U.S. Pat. No. 5,254,121 there is disclosed method and device for removing concretions within human ducts as the urethra or kidney. The device includes a flexible probe insertable through the human duct so that a tip thereof is juxtaposed against the concretion. The probe includes a positive electrode extending coaxially within the conduit and embedded in a solid insulation material. A negative electrode is coextensive with and outwardly encircles the positive electrode.

Relatively recently there have been developed medical lithotriptors which operation is based on so-called electro-impulse principle. This principle was adopted from mining technology, where it has been used for so-called high-power electro-impulse destruction of materials. This principle is based on the phenomena that applying of electrical impulses with the rise time of not more than 500 nanoseconds to two electrodes positioned on a solid mineral material immersed in water is associated with producing discharge, which does not propagate through the surrounding liquid medium, but rather through the bulk of the solid body itself. The electro-impulse technology was developed in late fifties in Russia and since then it was successfully implemented in such fields like crushing and disintegration of hard rocks and ores in mining industry, destructing of concrete blocks in building industry, drilling of frozen ground and extremely hard rocks, crushing of various inorganic materials, etc.

A survey of this technology can be found in a monograph "Basics of electro-impulse destroying of materials", by Semkin et al., Saint-Petersburg, Nauka, 1993.

According to this technology two or more electrodes are placed immediate on the surface of a solid body (rock) and very short impulses of voltage $U(t)$ are sent through them. Once an electrical breakdown between the electrodes is initiated, it occurs in the bulk of the solid body and is associated with producing of the breakdown discharge channel that extends within the bulk of the body.

The body itself serves as a medium to promote propagation of the electrical breakdown rather than the surrounding medium. Extension of the discharge channel through the body is accompanied by mechanical stresses, which stretch the body and destroy it as soon as the tensile strength of the body is exceeded.

In fact in the process of electro-impulse destroying the initiation and propagation of the discharge is similar to a micro explosion within the body.

It can be readily appreciated that since tensile strength of a rock is at least an order of magnitude less than its compressive strength, the electro-impulse crushing is associated with consumption of much less energy, than conventional electro-hydraulic crushing.

It has been also empirically established, that the probability of propagation of the breakdown channel through the body is higher when a very short voltage impulses are applied to electrodes, positioned on a solid body immersed in a liquid medium, since the voltage required for the breakdown within the bulk of the body is less, than the voltage required for breakdown within the liquid medium outside of the body.

Despite the fact that this technology exists for more than 40 years it has been employed mainly in mining and building industry for destruction of very large objects like rocks or concrete blocks as e.g. disclosed in WO 9710058.

The electro-impulse technology was only recently employed in medicine for lithotripsy treatment of calculi and a lithotriptor implementing this technology has been devised. This lithotriptor is manufactured by the company Lithotech Medical Ltd., Israel and is commercially available under the name Urolit. The method and apparatus for electro-impulse lithotripsy is disclosed in International application PCT/IL03/00191.

It should be pointed out that although the present invention is primarily an improvement referring to electro-impulse lithotripsy, nevertheless it can be implemented in other lithotripsy methods based on the principles listed above.

One of the problems associated with functioning of a lithotriptor energized by pulsed energy is erosion and mechanical wear of its probe. When pulses of energy are supplied to the working head of the probe its forwardmost end wears and damage can be caused to insulation of electrodes. As soon as the damage reaches certain limit repetitive use of the probe becomes ineffective, in the worst case, or it can be even dangerous for the personnel and for the patient. Therefore service life of the lithotriptor probe should not be too long and there exists certain limit, beyond which the probe has to be replaced.

There exist some prior art solutions attempting to cope with the problem of safety due to limited service life of the lithotriptor probe. The known in the art solutions are based simply on prolongation of the probe service life by using strong, wear resistant material for insulating the electrodes.

So, for example, in DE 3927260 there is disclosed electro-hydraulic probe, which working end is manufactured from ceramics having high mechanical strength.

In U.S. Pat. No. 5,254,121 is disclosed electro-hydraulic probe employing hard ceramic insulation around the electrodes, which reduces rate of wear and the working head of the probe is designed to reduce the influence of the discharging energy on electrodes.

In JP 3295549 is described electro-hydraulic lithotriptor with electrodes insulated by ceramic coating.

An alternative approach is based on controlling supply of energy supply to the probe to prevent achieving certain preset limit; otherwise operating of the system automatically terminates.

In EP 467137 is disclosed laser lithotriptor in which the energy emitted during operation of the laser is measured and controlled so as to keep it within a certain range.

The laser lithotripter comprises a calibration unit, a monitor unit and a measuring and control unit. During the dedicated calibration step, the energy emitted at the distal end of the probe is measured by the calibration unit and is compared with the energy emerging from the laser and measured by the monitor unit. During the treatment step, the measurement unit and control unit controls the laser operation on the basis of the energy values determined and set during the calibration step and on the basis of the current values determined by the monitor unit. In this system there is possible to control the preset operating parameters of laser during the instant treatment session such that the energy emanating from the probe does not exceed certain value which has been set at the calibration step. This principle of operation however would not be suitable for lithotriptors employing wearable probes since it does not take into consideration the energy supplied during the previous treatment sessions. The energy supplied during previous treatment sessions could cause wear to the probe before the instant session and therefore it should be taken into consideration for accurate estimation of the remaining service life of the probe.

In U.S. Pat. No. 6,264,653 is disclosed ablation catheter for creating long continuous lesions at targeted anatomical sites. The catheter is provided with a plurality of electrodes heated by pulsed radio frequency energy which is supplied to electrodes sequentially or continuously. The system and method is described which enables gauging the amount or quality of the contact between body tissue and one or more electrodes by counting the number of pulses delivered to a particular electrode and comparing it to the number of pulses supplied to at least one other electrode.

In wearable probes and especially those employed in electro-hydraulic or electro-impulse lithotriptors where pulsed energy is supplied to the probe it would be desirable to monitor the probe's service life continuously and assess it depending on the amount of previously delivered to the probe energy. This would allow deciding whether the remaining service life of the probe is still sufficient for its efficient and safe operation during the further treatment session or not. Furthermore, such monitoring would allow alerting and timely termination of the lithotriptor operation as soon as remaining service life of the probe approaches certain preset limit.

OBJECTS OF THE INVENTION

The main object of the present invention is to provide a new and improved method and system for destroying of undesirable formations in mammal body enabling to reduce sufficiently or to overcome the drawbacks of the known in the art solutions.

In particular the first object of the invention is to provide a new and improved method and system for intracorporeal lithotripsy based on supply of pulsed energy to a probe which working head is in contact with a formation to be destroyed.

Still further object of the invention is to provide a new and improved method of electro-impulse lithotripsy suitable for destroying of calculi appearing in a duct of a human.

Another object of the invention is to provide new and improved method and system for intracorporeal lithotripsy, suitable for continuous monitoring of the probe's service life to ensure reliable, safe and efficient operation of the probe during the treatment session.

Another object of the invention is to provide new and improved method and system for intracorporeal lithotripsy, enabling storing the amount of pulsed energy supplied to the probe during previous treatment sessions and terminating the system operation when the remaining service life approaches certain limit.

Yet another object of the invention is to provide new and improved method and system for intracorporeal lithotripsy, enabling reliable, safe and efficient operation of the probe irrespective of its diameter and irrespective of the parameters of the previously or currently supplied thereto pulsed energy.

Yet another object of the invention is to provide new and improved method and system for intracorporeal electro-impulse lithotripsy, enabling timely replacement of the worn probe when its remaining service life approaches certain limit.

Still further object of the invention is to provide a new and improved method and system for intracorporeal lithotripsy treatment enabling reducing probability for traumatizing of patient and/or personnel by virtue of alerting and automatic termination of the system when there is no grounding to the system control unit.

Still further object of the invention is to provide improved method and system for intracorporeal lithotripsy enabling display of the current operating parameters and of the remaining service life of the probe as well as alerting the personnel about approaching the limit set for the service life of the probe.

The above and other objects and advantages of the present invention can be achieved in accordance with the following combination of its essential features, referring to different embodiments thereof as a method for intracorporeal destroying of undesirable formation in a mammal body and as a system for implementation of the method.

According to an embodiment of the invention, which refers to a method it comprises:

In an embodiment of the invention referring to the system for intracorporeal destruction of an undesirable formation in mammal body by virtue of applying a pulsed energy to the formation it comprises:

a) Providing a probe insertable into mammal body, said probe having a working head, said probe is electrically connectable to a control unit, b) Bringing a forwardmost end of the working head in physical contact with the formation, c) Supplying pulses of energy from the control unit to the probe during at least one treatment session, d) Counting amount of pulses being supplied to the probe, e) Establishing a remaining service life of the probe by subtracting the amount of pulses being supplied to the probe from an amount of pulses corresponding to initial service life of the probe, f) Terminating the treatment session when amount of pulses being supplied to the probe approaches at least a fraction of the established remaining service life of the probe, g) Storing the established remaining service life of the probe.

The embodiment referring to a system comprises:

a probe insertable into mammal body, a control unit for supplying pulses to the probe and for monitoring and controlling amount of supplied pulses, a cable for electrical connection of the probe to the control unit and for supplying the pulses to the probe, said cable being detachably connectable to the probe by a coupler, wherein the system is provided with a memory means capable of storing information associated with at least a remaining service life of the probe, and there is provided a communication link between the memory means and the control unit.

The present invention has only been summarized briefly. For better understanding of the present invention as well of its embodiments and advantages, reference will now be made to the following description with reference to the accompanying drawings.

BRIEF DESCRIPTION OF THE DRAWINGS

FIG. 1b illustrates rear side of a control unit used in the system shown in FIG. 1a.

FIG. 1c illustrates an alternative embodiment of the system shown in FIG. 1a.

FIG. 5 is a block diagram of the system shown in FIG. 1a.

DETAILED DESCRIPTION OF THE INVENTION

Figure 1A:
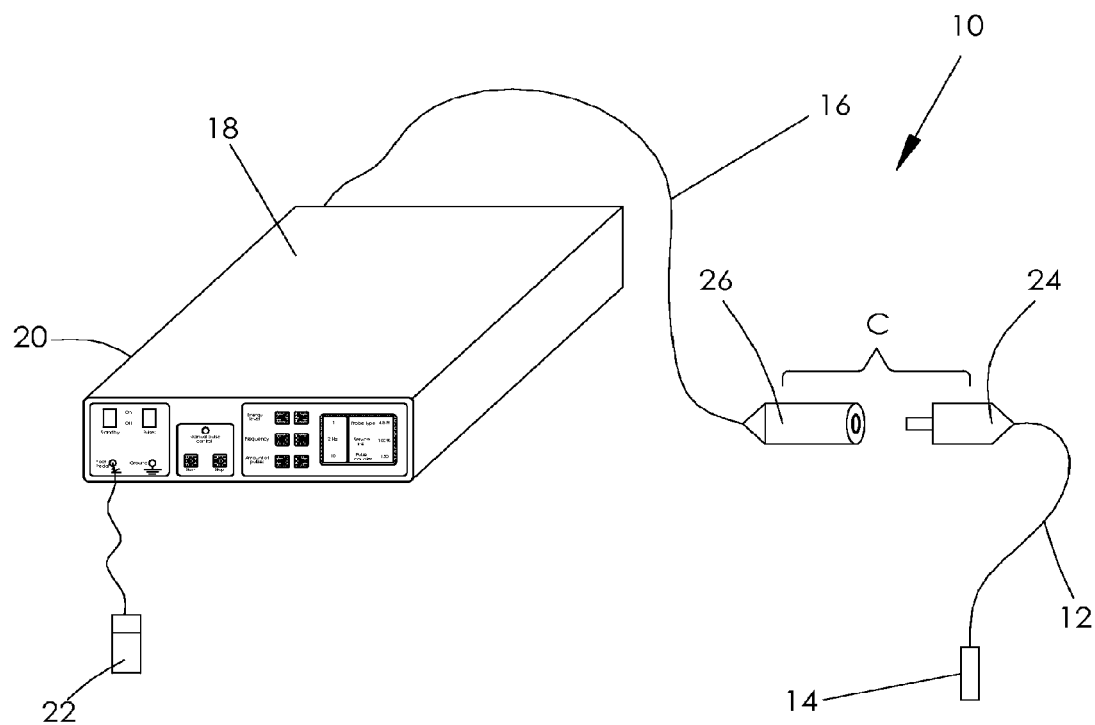
FIG. 1a shows general view of a system for intracorporeal destruction of an undesirable formation in a mammal body.

With reference to FIG. 1a an embodiment of the system of the invention is shown.

This embodiment and the further embodiments refer to intracorporeal destroying such formation like a calculus, which can be located for example in the biliary or urinary system of a human body. The system operates according to electro-impulse principle mentioned above and described for example in PCT/IL03/00191 the disclosure of which is hereby incorporated by reference. It should be borne in mind that other undesirable formations appearing in various ducts of a human body could be destroyed by the system as well.

In FIG. 1a is seen system 10 comprising a flexible probe 12 having a distal and a proximal end. At the distal end of the probe a probe working head 14 is fitted. Before initiating the treatment session the probe head is inserted into duct where the formation to be destroyed is located and forwardmost end of the working head is brought in physical contact with the formation. The proximal end of probe is detachably connectable to a cable 16, which in its turn is electrically connected to a control unit 18 from which pulsed electrical energy is delivered to the probe head. The control unit is provided with a housing 20 accommodating the components necessary for generating electrical pulses defined by electrical parameters suitable for efficient destroying the undesirable formation as required for example during electro-impulse intracorporeal lithotripsy. When the probe is connected to the cable it is possible to deliver the pulsed energy from the control unit to the probe working head. In practice when the system operates according to electro-impulse principle the pulses of energy supplied to the probe head from the control system are being defined by duration time of not more than 5000 nanoseconds, impulse rise time less than 50 nanoseconds, impulse energy of at least 0.01 joule and impulse amplitude of at least 2 kV.

The preferred configuration of impulses is rectangular and they can be supplied during treatment session either discretely as one time impulses or as series of repeating pulses with parameters preset by the control unit.

The control unit is provided with a foot pedal 22, electrically connected preferably to a front side of the control unit. By pressing on the pedal an operator can initiate generation of discrete pulses or one or more series of pulses and send the pulsed energy with required parameters to the working head of the probe.

The probe is detachably connectable with the cable by a coupler C, which comprises a male portion 24 associated with the proximal end of the probe and a female portion 26 associated with the cable. In FIG. 1a the coupler is shown in disconnected state, i.e. the male portion is separated from the female portion. One can readily appreciated that for operation of the system the male portion is inserted in the female portion to bring the coupler in connected state. The coupler will be disclosed in more details further.

Since during treatment session the probe head wears, the probe should be periodically replaced. Furthermore, some times it might be required to replace probes to allow using probes with different diameters. Detachable connecting of the control unit and the probe makes possible timely, convenient, fast and easy replacement of the probe.

At a front side of the control unit housing there are provided various indicators and knobs for setting the required parameters of the pulsed energy delivered to the probe. Those indicators and knobs will be explained further.

Figure 1B:
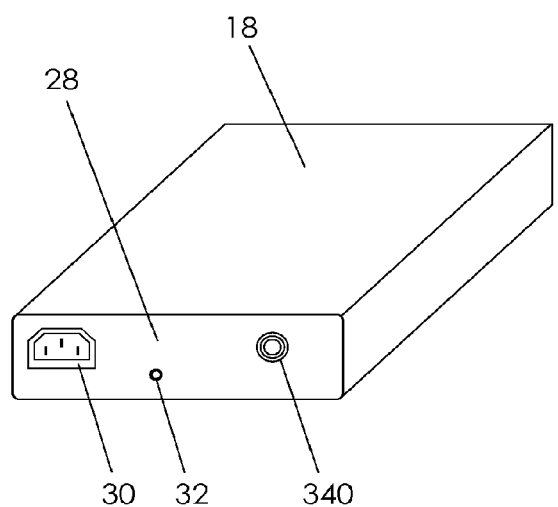

As seen in FIG. 1b at a rear side 28 of the control unit housing there is provided an electric outlet 30 for electrical connecting the control unit to a source of feeding voltage, a contact 32 for grounding the control unit housing and a port 340 for electrical connecting the control unit with cable 16.

In accordance with the invention when the probe is connected to the cable there is established a power line and a signal line between the probe and the control unit thus enabling delivery of pulsed electrical energy to the probe and exchange of information. The power line is implemented as a high voltage coaxial cable, while the signal line can be implemented as a miniature coaxial cable.

Furthermore, in accordance with the invention the probe is provided with a memory means, which stores initially preset amount of pulses corresponding to initial (ultimate) service life of the probe and the probe's type. Since the memory means is connected by the signal line with the control unit it becomes possible to monitor the amount of pulses delivered to the probe during the treatment session and to update the stored value of the remaining service life by subtracting the amount of the delivered pulses. By virtue of this provision delivery of the pulsed energy to the probe in the course of further treatment session can be controlled such that probe's operation can be terminated as soon as updated remaining service life approaches certain preset limit. In this situation operator is alarmed that the probe is worn and it should be replaced by a fresh one. By providing possibility for timely replacement of the probe efficient and safe operation of the system is preserved.

Figure 1C:
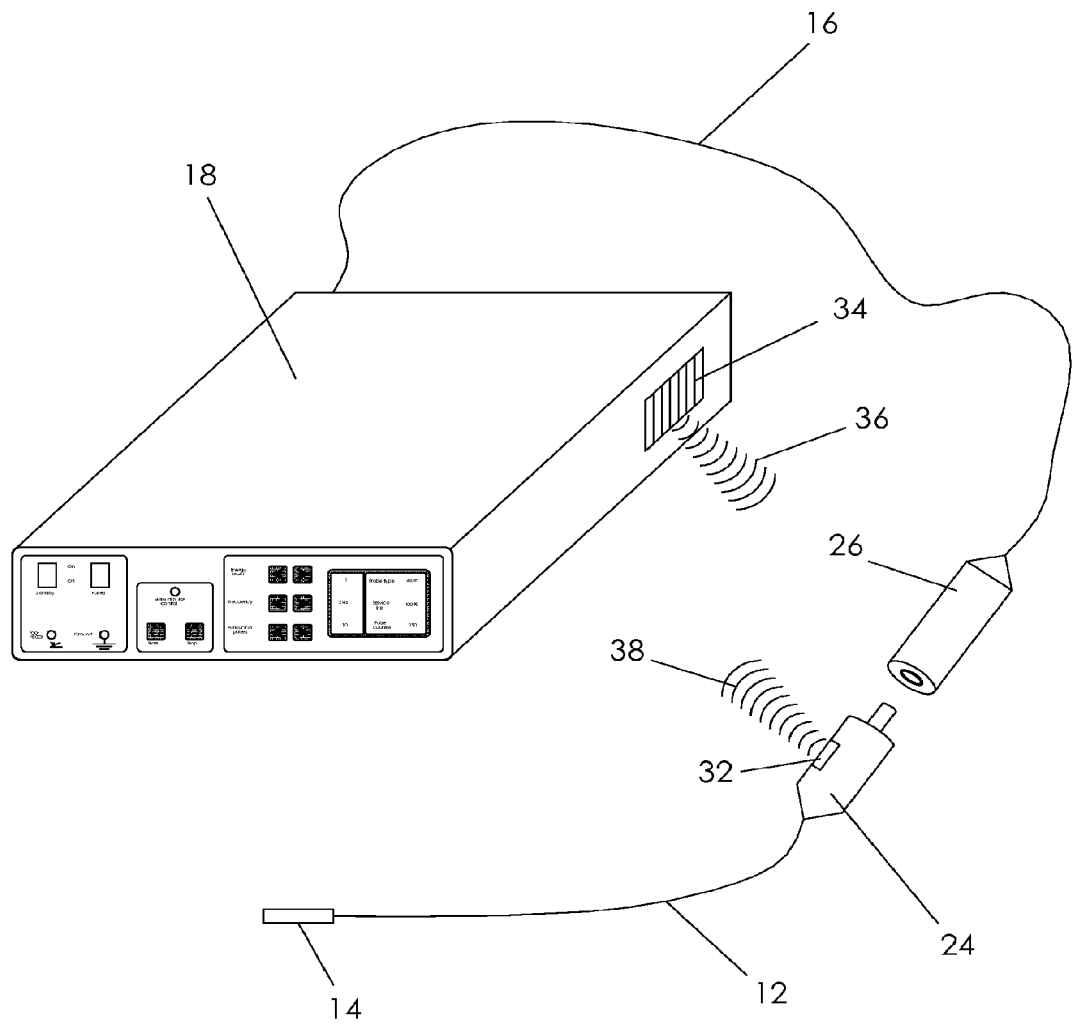

In FIG. 1c there is depicted another embodiment of the system, in which instead of a miniature coaxial cable for the signal line a wireless link is established between the probe and the control unit. This link can be implemented by providing the male portion 24 of the coupler with a transceiver 32 and the control unit 18 with a transceiver 34, which communicate by emanating and receiving respective signals 38, 36. For example transceiver 32 can be a programmable RFID tag programmed with identification information referring to the probe, its diameter, the current value of remaining service life and other identification information. The transceiver 34 can be appropriate interrogator/reader capable to communicate with the RFID tag. The wireless communication link may include any type of link, e.g. infra-red, radio wave or microwave wireless communication link.

One should readily appreciate that in the case of wireless communication between probe and control unit the cable 16 provides merely power line through which pulsed energy is delivered from the control unit to the coupler.

Figure 2:
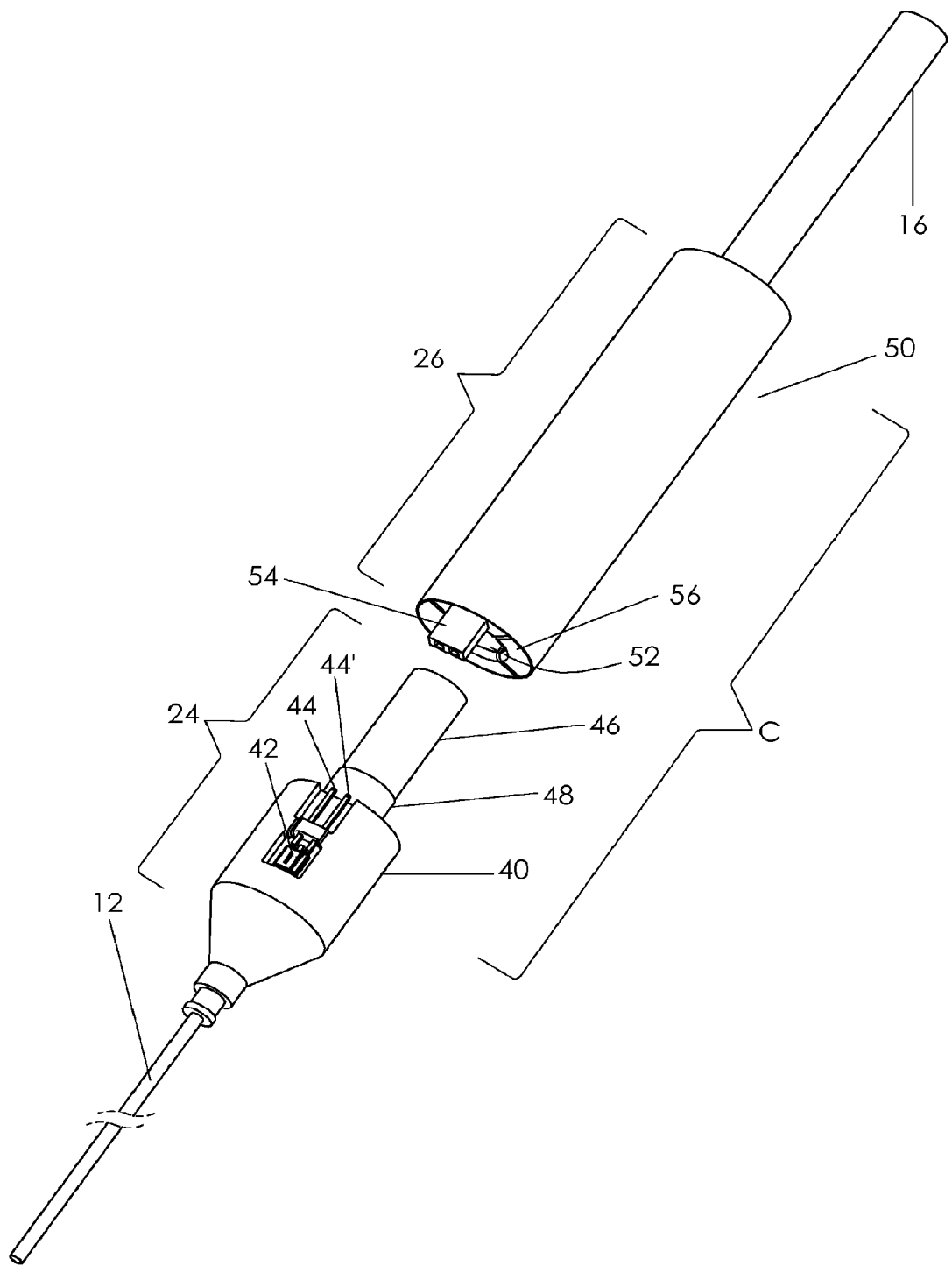
FIG. 2 depicts an isometric exploded view of a coupler connecting between probe and the control unit.

In FIG. 2 there is depicted an exploded view of the coupler C when it is in disconnected state. The coupler comprises male portion 24 connected to proximal end of the probe 12 and female portion 26 connected to distal end of the cable 16.

The male portion and the female portion are designed to be connectable and disconnectable.

The male portion is fitted with a housing 40, in which is received a memory means 42 provided with a couple of connecting contacts 44, 44'. The male portion is provided also with a high voltage insulator portion 46 protruding towards the female portion 26. The male portion is provided with a ground contact 48.

The female portion is provided with a housing 50 having longitudinally directed opening 52 in which the insulator portion 46 is received when the coupler is in connected state. The female portion is also provided with an electric outlet 54, in which the contacts 44, 44' are received when the coupler is in connected state.

The high voltage insulator portion is made of a dielectric material suitable to insulate electrically the inner coaxial electrode of the coupler from the outer coaxial electrode. The inner electrode is not seen in FIG. 2, but is shown with reference to FIG. 4a.

It can be appreciated that when the coupler is in connected state, i.e. the insulator portion is received within the opening 52, the inner electrode of the coupler is electrically connected to a core electrode of the cable connecting the coupler and the control unit, while the outer electrode of the coupler is electrically connected to a shield electrode of the cable. By virtue of this provision there is established power line between the probe and the control unit. At the same time when contacts 44, 44" are received in electric outlet 54 there is established signal line between the probe and the control unit.

Figure 3:
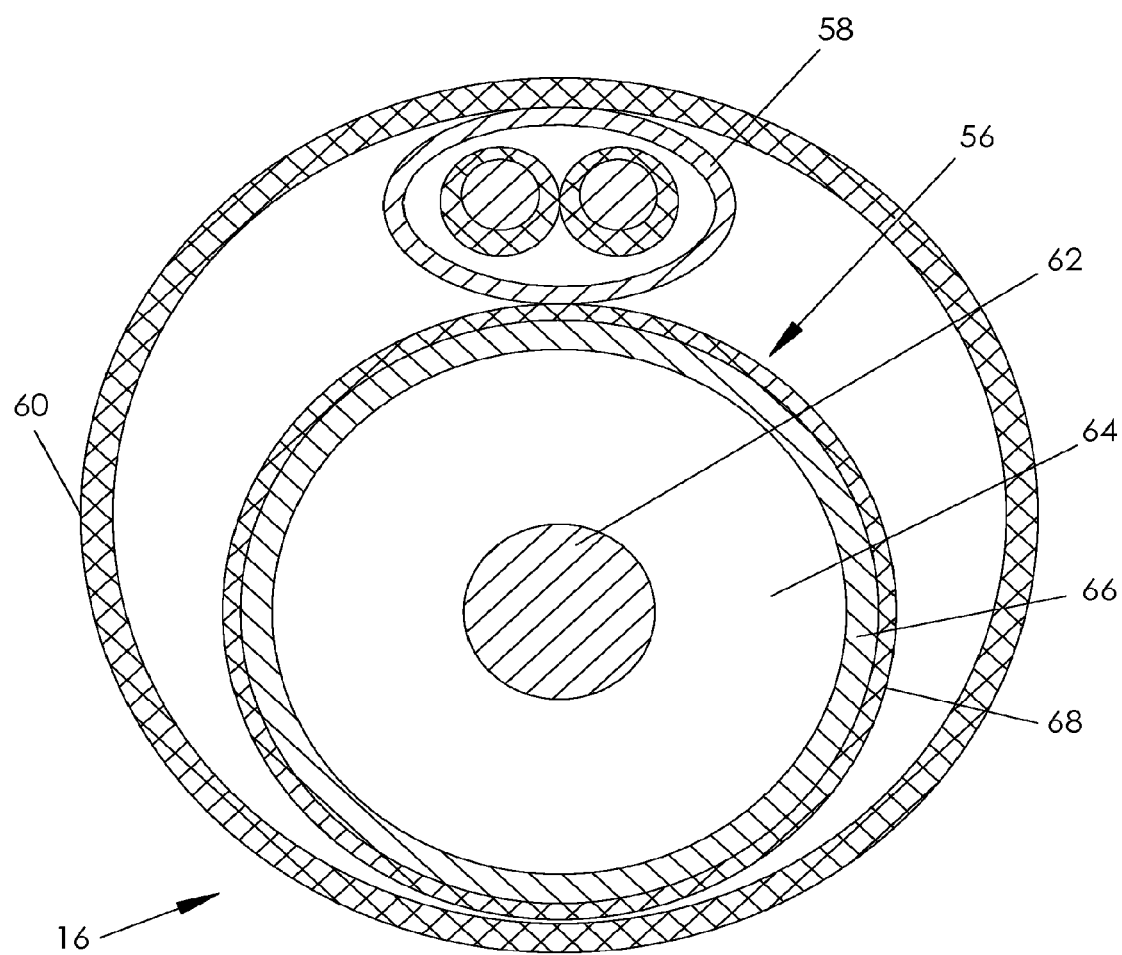
FIG. 3 is schematic cross sectional view of a cable electrically connecting the probe and the control unit.

Referring now to FIG. 3 there is shown cross sectional view of the cable 16, providing power line via a high voltage coaxial cable 56 and signal line via miniature coaxial cable 58. Both the high voltage power cable 56 and the miniature signal cable 58 are enclosed within a common cover 60 made of a suitable plastic material having appropriate mechanical and dielectric properties, e.g. TEFLON, polyimide, polyurethane etc.

The high voltage cable constituting the power line is an electrical coaxial cable provided with a high voltage core electrode 62 electrically insulated by an insulation 64 from a shield electrode 66. The insulation is made of a suitable dielectric material, e.g. TEFLON or FEP or PTEE. The shield electrode is covered by an insulation jacket 68 made of a dielectric material, e.g. TEFLON or FEP or PTEE or any other suitable dielectric material, which is also mechanically resistant to shock waves developing during the lithotripsy treatment session.

The memory means is preferably a non-volatile, programmable memory chip, e.g., ROM, EPROM, EEPROM, RFID tag or flash memory. Before exploitation of the probe the memory means is loaded with information which identifies the probe, like its diameter and with its initial service life, which has been established empirically previously for the same type of probe. The value of the initial service life is empirically established at conditions when pulses with minimum energy with frequency of 1 Hz are delivered to the probe of a specific diameter. These conditions depend on the probe diameter and are selected arbitrary. The amount of pulses which causes damage to the probe is set as initial (ultimate) service life and this value is loaded in the memory means and stored therein before exploitation of the probe.

During exploitation of the probe the initial service life is updated after each delivered pulse and its updated value is stored. When the same probe is used in the new treatment session the stored value of remaining service life will be a fresh initial value, which in its turn will be updated after each pulse delivered in the coarse of the new treatment session.

Before each treatment session the stored in the memory means value of service life is corrected by the control unit so as to take into consideration the actual conditions of the treatment session in terms of energy level and frequency of pulses to be delivered. Thereafter, during the treatment session the control unit permanently corrects the initially stored service life by subtracting from the stored value the instant amount of actually delivered pulses. The remaining in the end of the treatment session amount of pulses is set by the control unit as remaining service life and is loaded and stored in the memory means for the future treatment session.

Figure 4A:
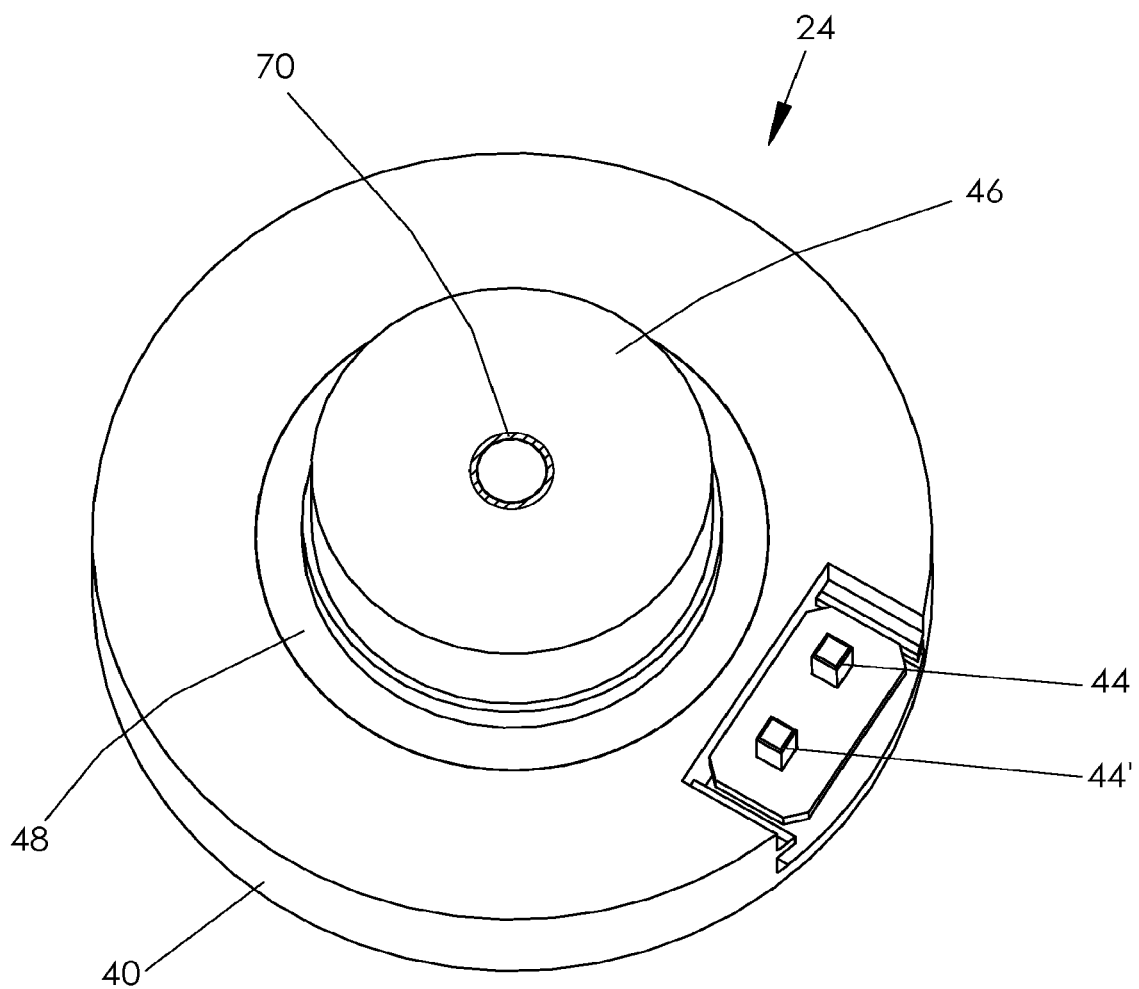
FIG. 4a is an enlarged isometric representation of a male portion of the coupler shown in FIG. 3.

Referring to FIG. 4a it is seen male portion 24 of the coupler fitted with housing 40, in which is deployed an inner electrode 70 surrounded by insulator portion 46. It is seen also an outer electrode, ground contact 48 and pair of contacts 44, 44' protruding from memory means 42 towards the female portion.

Figure 4B:
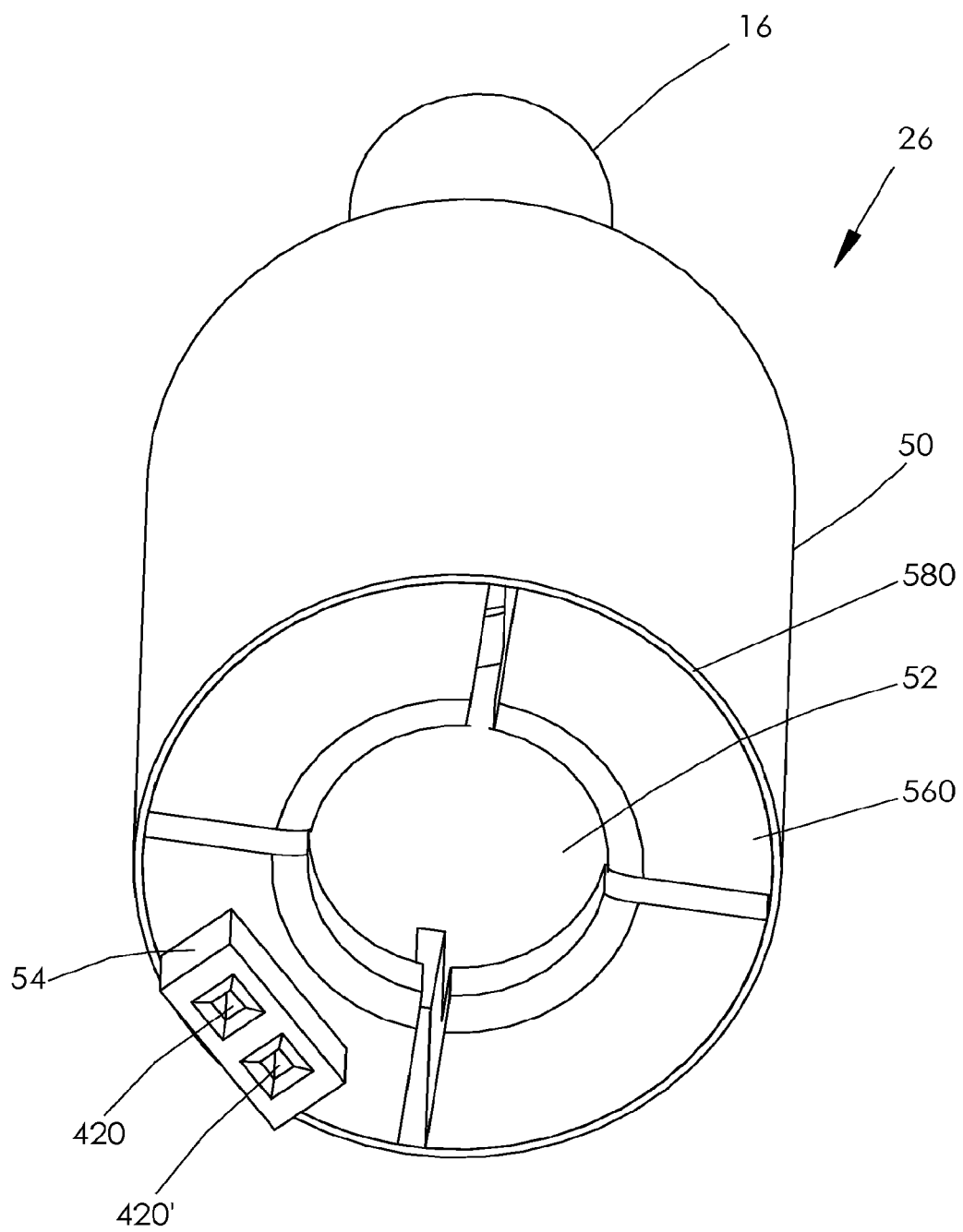
FIG. 4b is an enlarged isometric representation of a female portion of the coupler shown in FIG. 3.

In FIG. 4b there is depicted female portion 26 of the coupler having housing 50 surrounding a ground electrode 560 which is coated by an insulation jacket 580. The ground electrode is divided into four segments defining longitudinal opening 52 for receiving high voltage insulator portion 46. The ground electrode 560 is electrically connected to the shield electrode of the cable 16. The female portion is fitted with electric outlet 54 in which are made two depressions 420, 420' for receiving respective contacts 44, 44' of the male portion.

The male and female portion is configured and dimensioned such that when the male portion is connected to the female portion the insulator portion 46 is received within opening 52 and contacts 42, 42' are received within depressions 420, 420'. By virtue of this provision there is established power line and signal line between the probe, the cable 16 and the control unit such that pulsed energy can be delivered to the probe and its service life can be monitored and controlled by the control unit.

Figure 5:
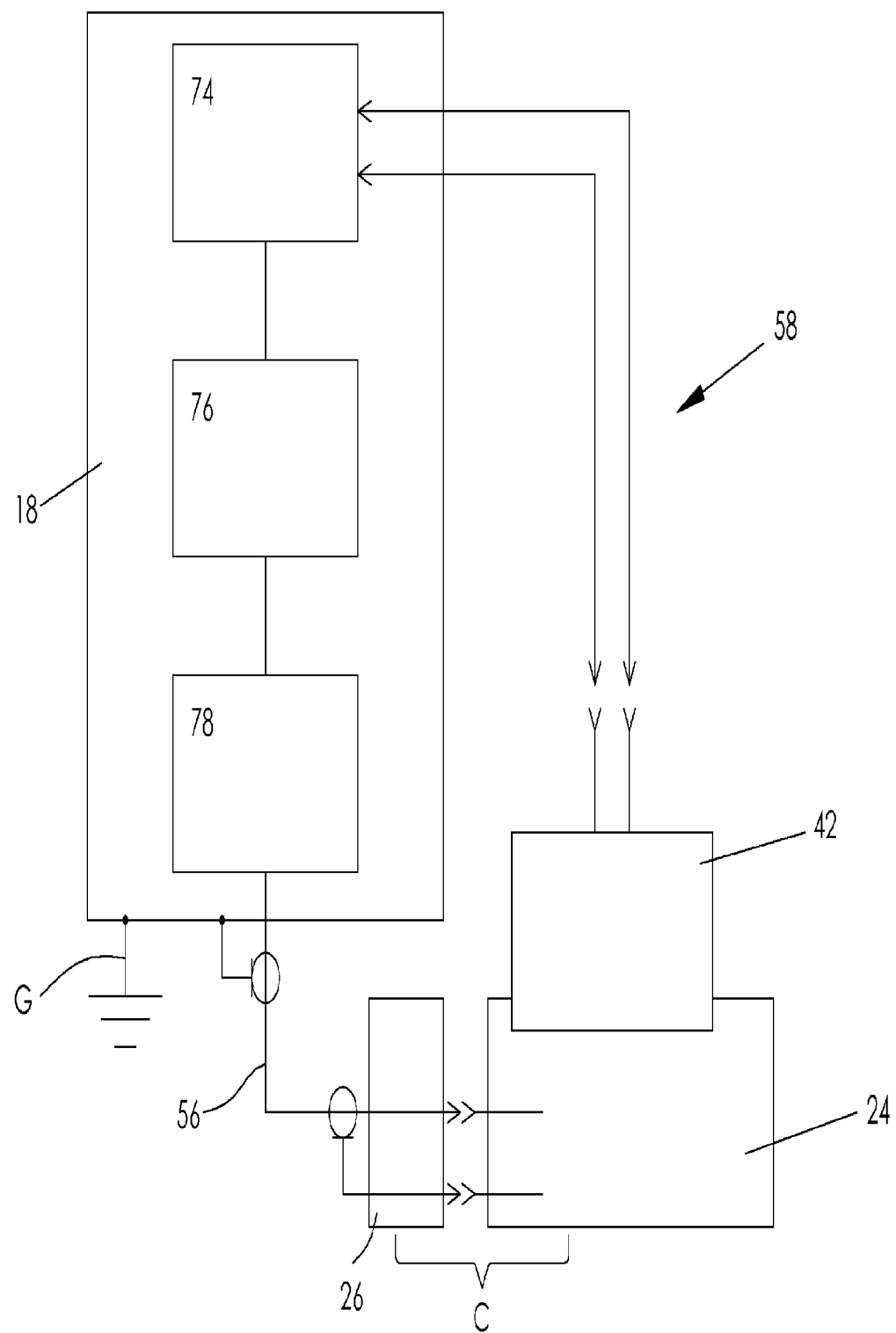

With reference to FIG. 5 control unit 18 is seen, which is electrically connected via coaxial power cable 56 with female portion 26 of coupler C. The control unit is also electrically connected by coaxial signal cable 58 with memory means 42 deployed in male portion 24 of the coupler. The portions of the connector are depicted schematically as being detachably connectable. Within the control unit are deployed various electronic and electric components, which enable inter alia generation of pulses, control of parameters of pulses, monitoring of remaining service life of the probe, calculating new value of remaining service life and its updating in the memory means. The housing of the control unit is provided with grounding G which status is automatically checked before initiation of a treatment session. The control unit is also provided with an alarm, which advises an operator when remaining service life approaches certain preset value and/or when the service life is exhausted.

Among the most important components of the control unit is a main control block 74, an auxiliary control block 76 and a generator of pulses 78. The main control block is responsible for checking the grounding, for controlling operation of the generator of pulses via auxiliary control block 76. The main control block is also responsible for reading the data stored in the memory means, like type of the probe and its stored remaining service life. Furthermore the main control block is responsible for calculating the updated value of the service life and loading thereof into memory means. The main control block is also responsible for passing parameters of the delivered pulsed energy and remaining service life of the probe to a display provided on the front side of the control unit housing.

Figure 6:
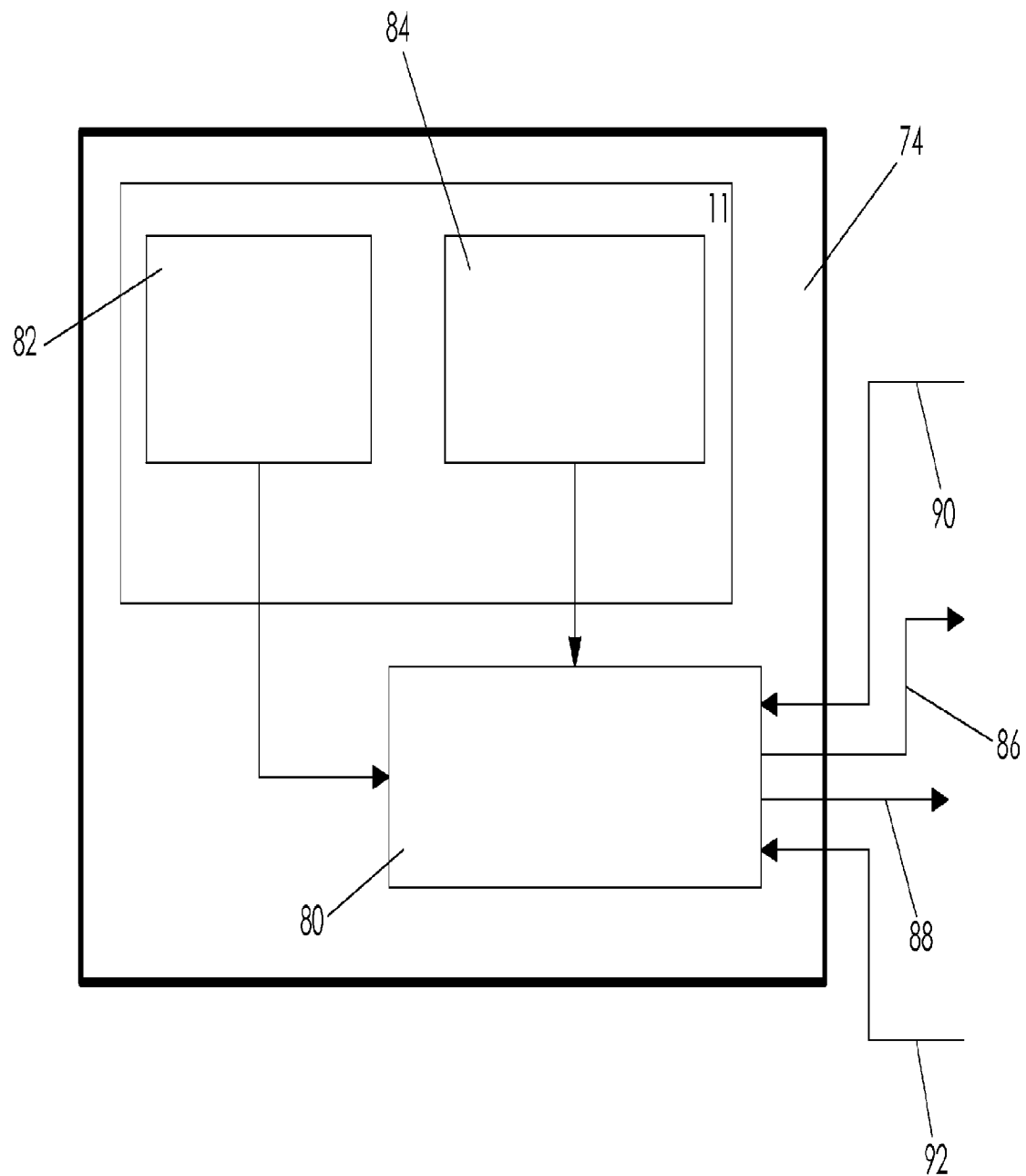
FIG. 6 is a generalized block diagram of the control unit.

FIG. 6 schematically shows enlarged diagram of the main control block having various entrances and exits for connection with other components which are required for proper fulfilling the above tasks.

The main control block 74 is provided with a microcontroller 80, e.g. Atmel MEGA32, manufactured by Atmel Corporation. The main control block comprises also a graphical user interface (GUI) with a display means 82 and an input means 84 enabling setting parameters of the pulsed energy. The main control block is provided with a digital exit 86 for exchange of information with the memory means, with an electrical exit port 88 for communication with auxiliary control block 76, with an electrical entrance port 90 for communication with a ground circuit and with a digital entrance port 92 for connection with generator of pulses 78 and for registering the amount of pulses delivered to the probe during treatment session.

Figure 7:
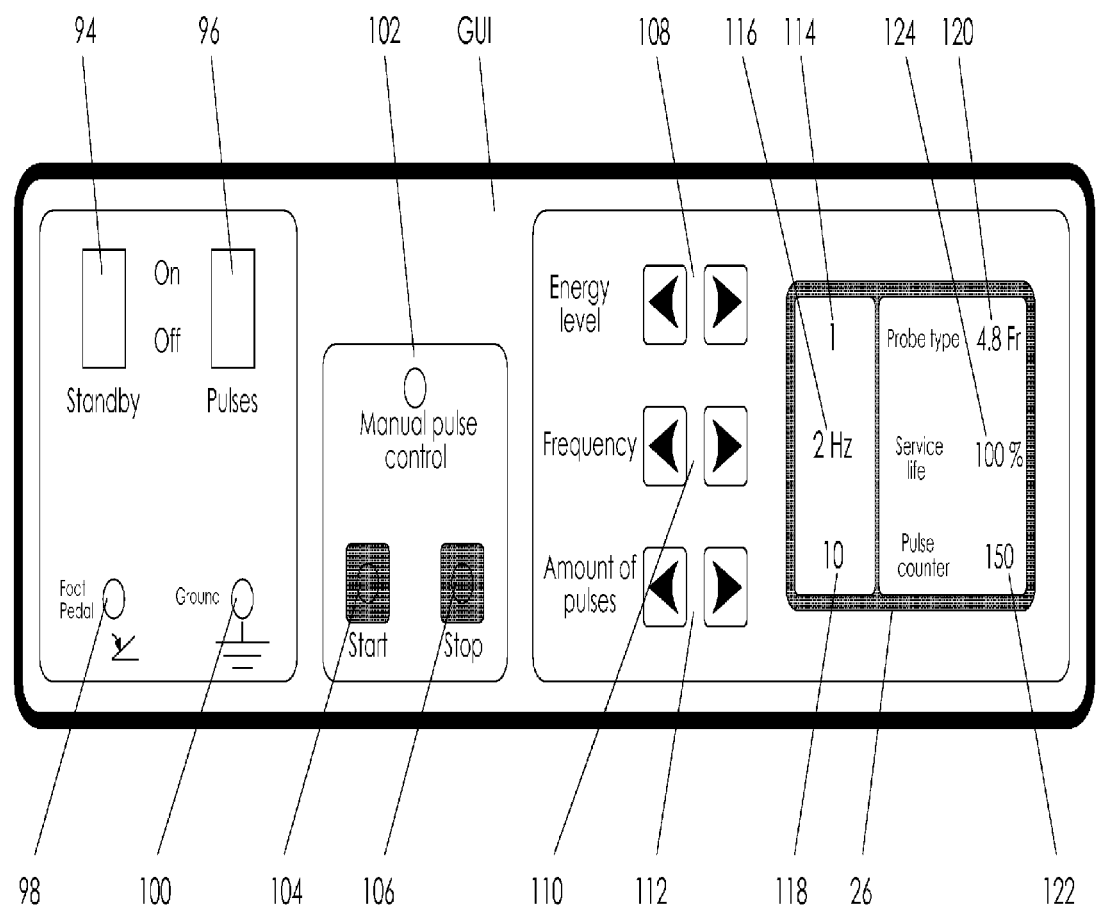
FIG. 7 illustrates front panel of the control unit.

Now with reference to FIG. 7 the display means and the input means will be explained.

On the front side of the housing 20 there is arranged graphical user interface GUI comprising various switches, knobs and indicators, which together constitute the display means and the input means. The input means for example comprises a main switch 94 for energizing the system, a switch 96 which allows for manual switching on and off of the generator of pulses. The display means comprises inter alia a LED indicator 100 for indicating status of the grounding and a LED indicator 102 for checking status of the foot pedal or manual switch 96, The input means further comprises knobs 104, 106 for starting and stopping the manual pulse initiation mode, a couple of knobs 108 for setting energy level of the pulsed energy, a couple of knobs 110 for setting frequency of the pulsed energy and a couple of knobs 112 for setting amount of pulses within a series (when the energy is delivered as series of pulses). At the right are provided respective LCD indicators 114, 116, 118, which indicate visually the parameters which have been set.

The further group of LCD indicators comprises a display 120 informing about diameter of probe in Fr, a display 122 informing about amount of pulses delivered during treatment session and a display 124 for indicating remaining service life of the probe.

In practice the energy of pulse can be set as an arbitrary number, e.g. in a range from 1 to 8, which corresponds to the range of energy used during the treatment.

The frequency of pulses delivered as a series can be set in a range, for example from 1 to 10 Hz. The amount of pulses in series can be set from 2 to 99.

The remaining service life of the probe can vary from 100% to 0%.

In addition to the information mentioned above the GUI alarms about a situation when during the treatment session there is suddenly no electrical connection between the probe and cable. In this situation the control unit stops generator of pulses and may generate an audio and/or visual alarm signal. Indicator 120 displays warning "NO PROBE" and indicator 122 displays blinking figures "00%". The audio and/or visual alarm may be also initiated when replacement of the probe was erroneously initiated during operation of the system.

Furthermore, the main control block may be designed to terminate operation of the system and prevent generation of high voltage pulses when there is no grounding to the housing of the control unit.

Figure 8:
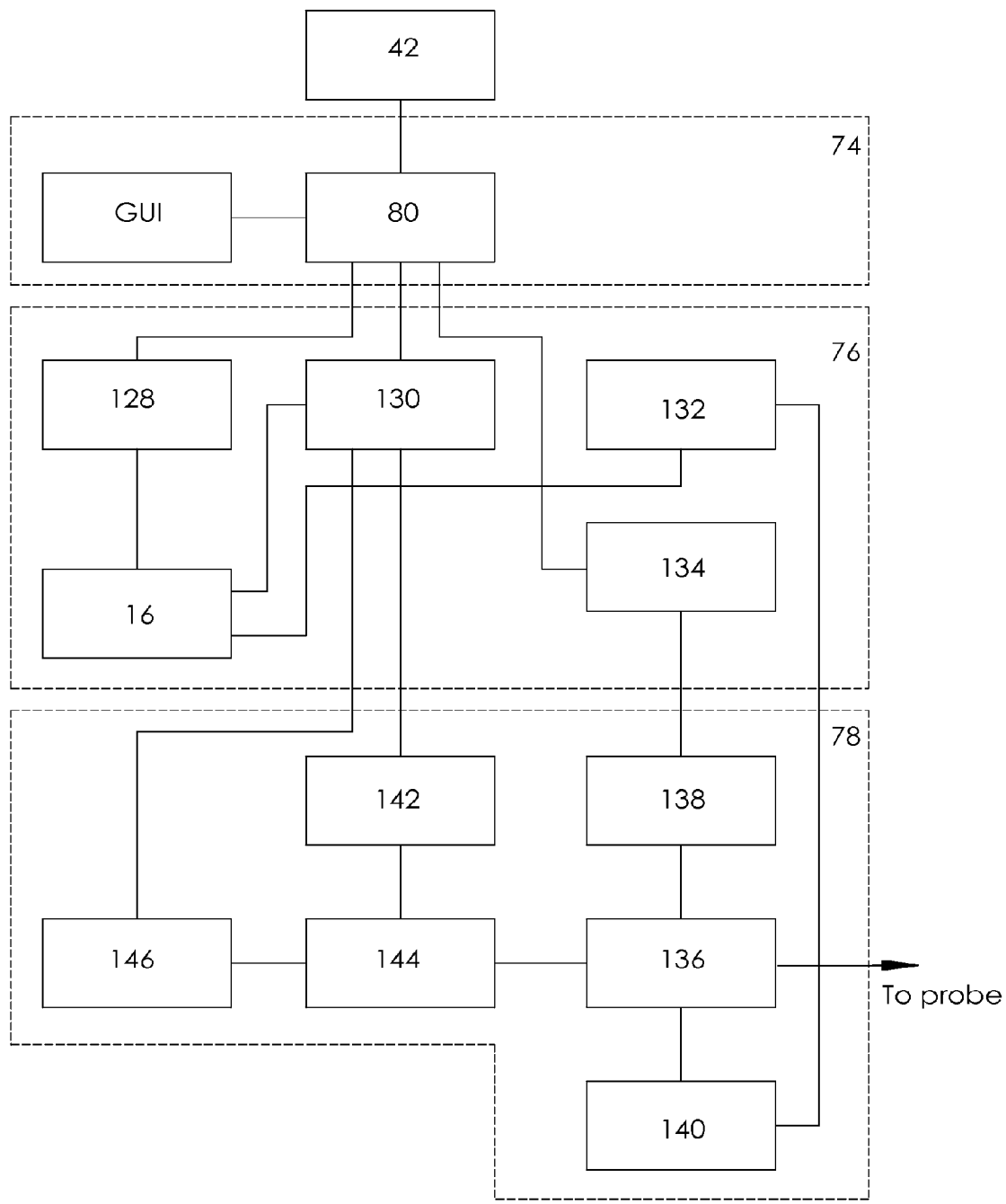
FIG. 8 is detailed block diagram of the system.

Referring now to FIG. 8 the block diagram of the system will be explained in more details. The block diagram shows memory means 42, main control block 74, auxiliary control block 76 and generator of pulses 78. The main control block and the auxiliary control block are configured as separate cards which are deployed along with other electronic components within the housing of the system control unit.

The main control block comprises microcontroller 80 and GUI.

The auxiliary control block comprises a low voltage feeding power source 16, a grounding control circuit 128, a high voltage power source 130, a thyratrone filament circuit 132 and a circuit 134 for starting the thyratrone.

The generator of pulses comprises a switching means 136, which preferably is a thyratrone, a transformer 138 for starting the thyratrone, a transformer 140, a high-ohmic divider 142, storage means comprising plurality of capacitors 144 and a rectifier 146. Instead of thyratrone one can use other switching means, which is known in the art of spark-gap control, e.g. transistors, thyristors etc.

Upon switching the system and the pulse generator on the microcontroller initiates the source of high voltage 130 and capacitors 144 are being charged up to a value that has been previously set up by energy level knobs 108. When this value is reached a comparator of voltage that is provided in the auxiliary control block sends a signal to microcontroller advising that capacitors have been charged sufficiently. The microcontroller produces a signal which terminates the charging process and a signal which initiates starting circuit 134 and transformer 138. The thyratrone generates pulse with particular parameters required for electro-impulse lithotripsy, for example as in the already mentioned International application PCT/IL03/00191. The pulses are passed to probe via cable 56. Upon producing the pulse and discharging the capacitors the comparator of voltage sends appropriate signal to the microcontroller which in its turn counts the amount of produced pulses and calculates the remaining service life of the probe as will be disclosed further.

The calculated value of remaining service life is sent by microcontroller via wire or wireless signal line to the memory means and is stored therein instead of the previously stored value.

The thyratrone starting circuit comprises a timer-microchip connected by its output to the power key (field transistor) in order to control thyratrone transformer 138. The thyratrone filament circuit comprises a step-down voltage converter with an adjustable output voltage stabilizer and an inverter. The thyratrone starting circuit is connected to the inverter.

Figure 9:
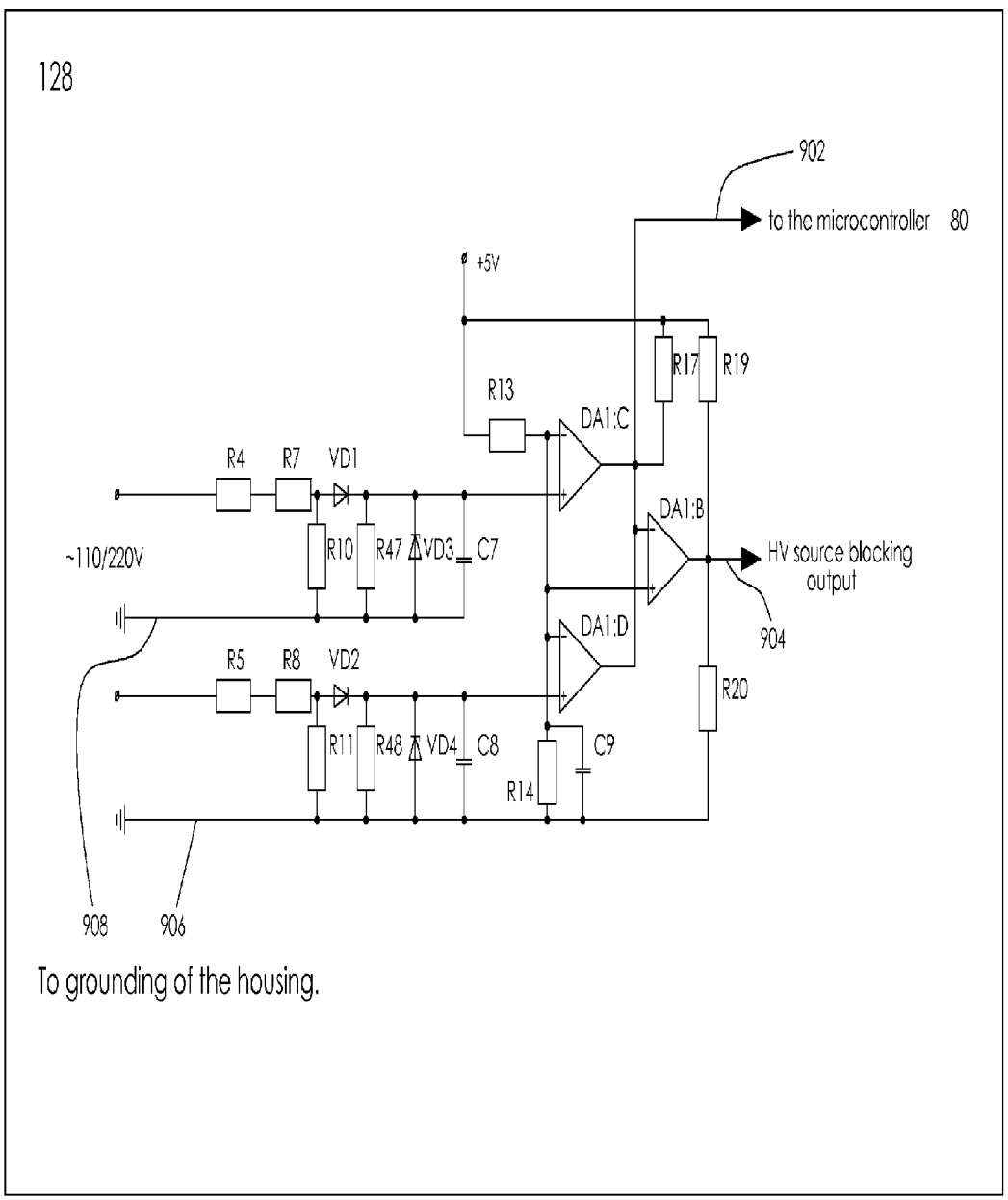
FIG. 9 presents a grounding control circuit.

One of the microcontroller's functions is controlling the circuit 128, which is shown in details in FIG. 9. By virtue of this provision the system operates safer. The grounding control circuit 128 may be designed as two high-ohmic dividers comprising respective resistors R4, R7, R10 and R5, R8, R11, respective rectifiers VD1, VD2, respective stabilizers VD3, VD4, respective capacitors C7, C6 and comparators DA1.B, DA1.C, DA1.D. Exits of comparators DA1.C and DA1.D are electrically connected by line 902 to microcontroller 80. Exit of comparator DA1.B is electrically connected to high voltage power source 130. The dividers are electrically connected both to the power source 16 and by lines 906, 908 to the housing of the system control unit. The first divider's phase line and the second divider's neutral line are connected to the housing. Fed by source 16 the AC voltage is reduced by the dividers, rectified and then supplied to the comparator' inputs where both "phase" and "neutral" voltage levels are compared with regard to the housing. The housing of the control unit is considered grounded unless both voltages are present. The outputs of comparators DA1.C and DA1.D are connected to line 902 using a logical OR circuit and generate a logical signal for the microcontroller to either allow or block the pulse.

DA1.B comparator also generates an additional signal which may be passed through dedicated line 904 to high voltage source 130 to block its operation. The high voltage source which charges capacitors 144 to the preset voltage levels may be designed as a backlash converter circuit comprising a driver microchip, a power key (field transistor), step-up transformer with a rectifier, and a high-ohmic divider with a digital potentiometer in the feedback circuit.

The electric resistance level of the digital potentiometer is set by the microcontroller. Also it allows charging the capacitors by sending the control signal to the driver microchip. Comparator of voltage connected in parallel to the driver microchip determines whether the capacitors are sufficiently charged or not. The signal generated by this comparator is an information signal for the microcontroller to clock the start-stop of the high voltage source, which initiates pulse generation and counting the number of generated pulses.

Power source 16 energizes all functional units of the auxiliary control block.

Now with reference to FIG. 10 it will be explained the operation of the system and in particular the method of monitoring and updating the remaining service life of the probe. The initial service life is established according to coefficient A, which is energy level and coefficient B, which is frequency of the pulses to be produced. In the course of treatment session the initial service life is recalculated by subtracting from the initial value the amount of produced and delivered pulses. The resulting amount of pulses is taken as remaining service life of the probe.

The initial service life is expressed as $N_{A,B}=N_{1,1}\times(A\times B)$, where $N_{1,1}$ is the amount of pulses delivered to the probe at minimum energy level (for the probe of given diameter) at frequency of 1 Hz. This amount is established empirically for each probe's type during its manufacturing. The established value is stored in the memory means. Parameters A and B are dimensionless normalization coefficients, which depend on energy level and frequency and are used for normalization of the remaining service life. Those coefficients are also established empirically and stored in the memory means. In the table 1 and 2 below are listed coefficients A and B depending on energy level and frequency. The energy levels are arbitrary divided into 8 levels from 1 to 8. The frequency refers to a series of pulses with 1 to 5 pulses in one series.

TABLE 1

Coefficient A depending on energy level.

| Energy | 1 | 2 | 3 | 4 | 5 | 6 | 7 | 8 |
|---|---|---|---|---|---|---|---|---|
| A | 1 | 0.8 | 0.8 | 0.6 | 0.6 | 0.5 | 0.4 | 0.4 |

TABLE 2

Coefficient B depending on frequency.

| Frequency, Hz | Discrete pulse | 1 | 2 | 3 | 4 | 5 |
|---|---|---|---|---|---|---|
| B | 1 | 1 | 0.9 | 0.9 | 0.8 | 0.8 |

The calculation of the initial service life is carried by the microprocontroller.

For example for a certain probe the stored N1,1 value is 1000 pulses and during the treatment session it is required to produce series of pulses at energy level 8 and with frequency 5 Hz. Series of pulses is a pulses quantity given by an operator. This quantity is pre-settable and can be changed from 2 till 99. The system allows producing the pre-set quantity of pulses by pressing foot pedal or knob. It is possible to terminate operation of the system by releasing pedal or knob. Also the system can operate in a single pulse mode, when discrete pulses are produced upon pressing pedal or knob.

The normalizing parameters A and B will be 0.4 and 0.8 respectively and the initial service life at the above conditions will be N8,5=1000×(0.4×0.8)=320 pulses. This means that each 3.2 pulses would reduce the initial service life by 1 percent.

At the same time when the probe produces pulses with energy level 1 and at frequency 1 Hz the initial service life is N1,1=1000 pulses. This means that each 10 pulses would reduce the initial service life by 1 percent.

During operation of the system microcontroller of the control block 74 counts produced pulses and calculates the remaining service life after each produced pulse while taking into consideration its normalized weight depending on parameters A and B. The calculated value is stored in the memory means. This fresh value updates the previously stored value of the initial service life. The amount of delivered pulses, their parameters and updated value of the remaining service life rounded off to full percents is displayed on the front panel. The main control block terminates operation of the system when remaining service life is exhausted. The microcontroller of the main control block can be programmed to terminate the system even before exhausting the remaining service life. This can be accomplished by setting a certain limit for the remaining service life, e.g. 10 percents. In this situation as soon as remaining service life approaches 10% the system stops and alarms audibly and/or visually about terminating the operation of the system. The system can be initiated again and it operates until full exhausting the remaining service life. In this situation the system stops and produces alarm.

Figure 10:
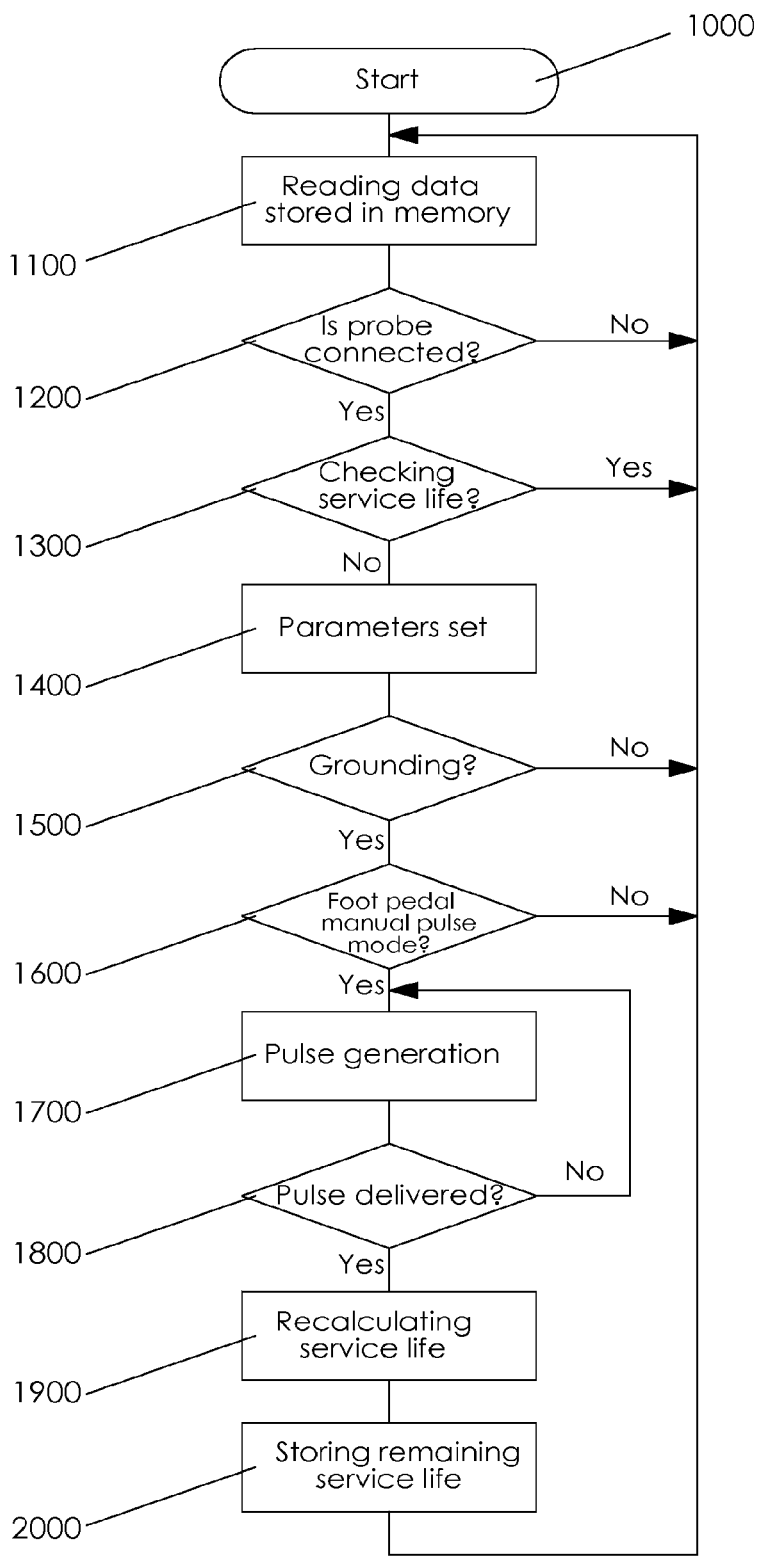
FIG. 10 is a flow chart showing operation of the system.

Referring now to FIG. 10 it is shown an algorithm according to which operates the system for monitoring and controlling the remaining service life. At a step 1000 the system is initiated and starts working. This is accomplished by connecting net connector 30 to source of feeding voltage and turning on the main switch 94. During this step the microprocontroller checks status of the input means, and of the grounding control circuit. Then at steps 1100 and 1200 the microcontroller respectively checks the content of the memory means and whether the probe is connected to the control unit. The microcontroller reads information stored in the micro chip of the memory means. If the probe is not connected the control block prevents operation of the system. If the probe is connected a next step is carried out as denoted by numeral 1300. At this step the microcontroller checks the remaining service life of the probe. If it is exhausted the control block prevents operation of the system. If it is not exhausted yet a next step is carried out as denoted by numeral 1400. At this step the required pulse parameters are set. This is accomplished by knobs 108, 110, 112. Upon setting the parameters a next step is carried out, which is checking the grounding as denoted by numeral 1500. This step is accomplished by grounding control circuit 128. If there is no grounding to the housing of the control unit the main control block keeps the system waiting and prevents generation of pulses. If the grounding is OK the next step can be carried out as denoted by numeral 1600. At this step the main control block checks status of foot pedal 22 and of knob 104.

If neither the pedal nor the knob is pressed the system is kept waiting. If one of them is pressed the system can carry out a next step as denoted by numeral 1700, which is generation of pulses with parameters set at step 1400. Generation of pulses is effected as described above in connection with the main control block and the auxiliary control block.

At a next step, which is denoted by numeral 1800 the main control block checks whether the pulse has been delivered to the probe. If the pulse has not been delivered the system will be urged to generate the pulse again. If the pulse has been delivered the next step is carried out as denoted by numeral 1900. This step comprises counting of the produced and delivered pulses and recalculating the remaining service life of the probe. The remaining service life is recalculated after each delivered pulse by the microcontroller, which uses the previously stored value of the remaining service life. The remaining service life is recalculated for the first treatment session and for each subsequent treatment session. For the first treatment session the microprocontroller uses stored value of the initial service life normalized according to coefficients A and B corresponding to parameters set during the step 1400. For the subsequent sessions the microprocontroller recalculates the remaining service life using the current stored value of the remaining service life. Upon recalculating the fresh value of the remaining service life is stored in the memory means and displayed on front panel of the control unit. This is accomplished at a step 2000.

Below are given examples of recalculation of the remaining service life for a single treatment session and for two subsequent treatment sessions.

Example 1

Flexible probe with diameter of the working head 2.7 Fr (0.9 mm) was used with the electro-impulse system Urolit. The initial service life of such probe type has been established with the aim of an auxiliary probe to which were delivered single pulses with energy level 1 (0.1 Joule) at frequency 1 Hz. The established value of the initial service life $N_{1,1}$ was 1000 pulses.

Parameters of the delivered pulses could be set as follows: selecting mode of pulse delivery (single pulses or series of pulses), energy level in the range of 1-8 (0.1-1.0 joule), frequency in the range 1-5 Hz, amount of pulses in the series in the range 2-99. Coefficients A and B presented in table 1 and 2 were used for normalization the initial service life and calculating the remaining service life.

For a single treatment session the following parameters were set:
a) energy level—5
b) frequency—1 Hz.

Therefore the initial service life for this probe at the above conditions would be $$N_{5,1}=1000 \times (0.6 \times 1)=600 \text{ pulses.}$$

During the single treatment session there were delivered 12 pulses with the above parameters and therefore the remaining service life which would be displayed after completing the session is:

$$[(600-12)/600] \times 100\% = 98\%.$$

Example 2

The probe with the same parameters as above was used for two subsequent treatment sessions. During the first session there were delivered 20 pulses with energy level 8 and at frequency 5 Hz. The initial service life of the probe for treatment session with the above parameters of pulsed energy would be $$N_{8,5}=1000 \times (0.4 \times 0.8)=320 \text{ pulses.}$$

After delivering 20 pulses the remaining service life in the end of the first session would be $[(320-20)/320] \times 100\% = 93.75\%$ and after rounding off the displayed value of the remaining service life would be 94%.

After completing the first treatment session the second session has been carried out during which there were delivered 18 pulses with the following parameters:
a) energy level—6
b) frequency—2 Hz The initial service life of the probe at those parameters would be:

$$N_{6,2}=1000 \times (0.4 \times 0.9)=360 \text{ pulses}$$

The remaining service life after completing the second session would be:

$$94-(18/360) \times 100\% = 89\%.$$

Thus by virtue of the system and method of the invention it becomes possible easily and conveniently to monitor the service life of the probe, timely replace it and therefore to render operation of the system more efficient and safe.

It should be appreciated that the present invention is not limited to the above-described examples and that one ordinarily skilled in the art can make changes and modifications without deviation from the scope of the invention, as will be defined in the appended claims.

So for example, the above-described algorithm as well as the system configuration could be implemented in other system which operation is based on delivery of pulses of energy but not necessarily according to electro-impulse principle.

It should also be appreciated that the features disclosed in the foregoing description, and/or in the following claims, and/or in the accompanying drawings may, both separately and in any combination thereof, be material for realizing the present invention in diverse forms thereof When used in the following claims, the terms "comprise", "include", "have" and their conjugates mean "including but not limited to".

The invention claimed is:

1. A system for intra corporeal electro-impulse destruction of an undesirable formation in a mammalian body by applying high voltage pulses of energy immediately to the formation, said system comprising:
    a treatment probe insertable into the mammalian body,
    a control unit suitable for generation of pulses of energy and for monitoring and controlling their amount as well as their energy and frequency,
    a power line for electrical connecting of the treatment probe to the control unit, said power line consisting entirely of a high voltage coaxial cable,
    wherein the system is provided with
    a memory means which is capable of storing information associated with a service life of the probe, wherein said information comprises at least a probe diameter,
    and said control unit is provided with a programmable microcontroller that stores a program for monitoring and controlling the service life of the probe and at least one normalizing coefficient which has been empirically established during supplying pulses of energy to an auxiliary probe
    and the system further comprises
    a communication link for exchange of information between the control unit and the memory means.

2. A system of claim 1, in which said control unit is capable to supply pulses of energy having duration not more than 5000 nanoseconds, pulse rise time less than 50 nanoseconds, pulse energy at least 0.01 joule and pulse amplitude at least 2 kV.

3. A system of claim 1, comprising a coupler for electrical connection between the probe and the control unit, said coupler is provided with a male portion and with a female portion.

4. A system of claim 1, in which said communication link is a wire link.

5. A system of claim 4, in which said wire link comprises a miniature coaxial cable.

6. A system of claim 3, in which said memory means resides in the male portion of the coupler.

7. A system of claim 1, in which said control unit comprises a source of low voltage, a grounding control circuit, a source of high voltage and a circuit for starting a fast operating switching means.

8. A system of claim 7, in which said fast operating switching means comprises a thyratron.

* * * * *